United States Patent [19]

Pauldrach

[11] Patent Number: 5,578,056
[45] Date of Patent: Nov. 26, 1996

[54] SEPARABLE ECONOMICALLY PARTIALLY DISPOSABLE FLEXIBLE BIOPSY FORCEPS

[75] Inventor: Georg Pauldrach, Garbsen, Germany

[73] Assignee: Ballard Medical Products, Draper, Utah

[21] Appl. No.: 360,887

[22] Filed: Dec. 21, 1994

[51] Int. Cl.$^6$ .................................................. A61B 10/00
[52] U.S. Cl. ...................... 606/205; 128/751; 128/754
[58] Field of Search ..................................... 606/205–209; 128/751, 754

[56] References Cited

U.S. PATENT DOCUMENTS 4,817,630  4/1989  Schintgen ........................... 128/751

FOREIGN PATENT DOCUMENTS 0225045  6/1987  European Pat. Off. ............... 606/205

*Primary Examiner*—Michael Powell Buiz
*Assistant Examiner*—Patrick W. Rasche
*Attorney, Agent, or Firm*—Workman Nydegger Seeley

[57] ABSTRACT

A biopsy forceps having a disposable cable formed by helically wound wire with distal and proximal ends. The helically wound wire forms a passage therethrough from the distal to the proximal end. The biopsy forceps includes a reusable forceps instrument assembly which has a control wire passing through the passage. A pair of sharpened jaws are located at the end of the control wire and are joined to a jaw mount by means of pivot. The jaw mount includes a socket for selective coupling and uncoupling to the distal end of the helically wound wire, by rotating the distal end of the helically wound wire into or out of the socket so that the helically wound wire of the support cable can be uncoupled from the jaw mount and discarded, while the forceps assembly, including the jaw mount together with the control wire and pivotally mounted jaws can be removed as an entire assembly and resterilized for use with another support cable.

3 Claims, 1 Drawing Sheet

SEPARABLE ECONOMICALLY PARTIALLY DISPOSABLE FLEXIBLE BIOPSY FORCEPS

FIELD OF THE INVENTION

Biopsy forceps with a flexible support cable, a jaw mount on the support cable with jaws, and a control wire to operate the jaws. The expensive jaw mount and jaws, and the control wire are readily removable from the support cable so the cable can be discarded, and the more expensive mount, jaws and control wire, may be cleaned and reused. Only the less expensive support cable need be replaced.

BACKGROUND OF THE INVENTION

Biopsy forceps for endoscopic usage characteristically include a pair of pivotally mounted jaws mounted at the distal end of a tubular support member. Rigid instrument constructions utilize a rigid tube for supporting the jaws. Flexible constructions utilize a flexible tubular cable for supporting the jaws.

Rigid instruments of this type tend to be more expensive, and are intended to be re-used. They are designed for this, and are rather easily cleaned and sterilized for their next use.

However, flexible instruments involve a different set of problems, one of which is the near impossibility of cleaning such instruments, especially when the jaw mount is permanently attached to the support cable. The internal dimensions and clearances are very small, and because the cables are tightly wound helical springs, it is impractical to reach the inside of the support cable to clean it. As a consequence, flexible biopsy forceps are usually discarded after a single use. The mount, the jaws, and the control wire are the greatest part of the cost of the instrument. The support cable is not very expensive, but the jaws are quite expensive because they are small, held to close tolerances, and have sharpened cutting edges.

Accordingly, if an arrangement can be made such that the jaw mount can readily be removed and replaced, then it along with the jaws and control wire which are attached to it can easily be cleaned. Then the inexpensive support cable can be discarded and replaced with a new clean one. The expensive parts of the instrument are thereby saved and re-used. The only cost for re-use is the small expense of a new support cable.

As simple as this objective sounds, it has not heretofore been attained because of the difficulty of removably attaching the mount to the resilient spring-wound support cable. The spring cannot be threaded, and it is impractical to form internal threads in the small jaw mount. Accordingly, the jaw mounts have been permanently affixed, such as by crimping, which prevents the mount from being removed and re-used. Such an instrument is not re-usable because it cannot be cleaned.

It is an object of this invention to take advantage of an inherent property of the support cable to enable a jaw mount to be removably mounted to a helically-formed support cable, and then be applied readily to another one.

BRIEF DESCRIPTION OF THE INVENTION

A biopsy forceps according to this invention includes a flexible tubular support cable with an internal passage. The support cable has a proximal end and a distal end.

A jaw mount is mounted to the support cable at its distal end. It supports a pair of pivoted jaws having sharp cutting edges that are moved toward and away from one another by a control wire. The control wire passes through the passage in the support cable. It connects to the jaws at the distal end.

The support cable and control wire are attached to actuation means such as a scissor type grip, or a thumb loop and handle. Both are well-known means for moving a control wire in a support cable.

According to this invention, the support cable is a tightly wound helical spring. It is made of a suitable metal, and of such dimensions that it can readily bend to conform to bends in a cavity into which it is inserted, such as the colon. Inherently, its outer surface has a helically shaped groove and crest, much like a helical thread. Because the support cable is inherently springy in the sense of deflectibility, it can be compressed radically (lengthening slightly to enable this), and will exert a spring-back force against a body tending to compress it.

It follows that if the mount has a tubular socket whose internal diameter is suitable smaller than the outermost diametrical dimension of the support cable's convolutions, and can be placed over them, then the jaw mount will be reliably retained.

The nearest known approach to this arrangement is to place the end of the support cable in a socket in the jaw mount with a net fit or an over-size fit, and crimp it in place. This destroys the jaw mount for re-use.

According to this invention, the socket makes an interference fit with the convolutions, and is placed over them by means of rotating it around the cable's axis so that the convolutions tend to "thread" their way into the socket even though the socket has no threads. In fact, it is cylindrical. Removal is the reverse—the mount is simply turned in the opposite direction.

Accordingly the jaws, jaw mount, and control wire, which are readily cleaned, can be re-used indefinitely, requiring only a new support cable each time. The instrument is taken apart to be cleaned and the jaw mount can readily be applied to a new support cable.

The above and other features of this invention will be fully understood from the following detailed description and the accompanying drawings, in which:

DETAILED DESCRIPTION OF THE INVENTION

Figure 1:
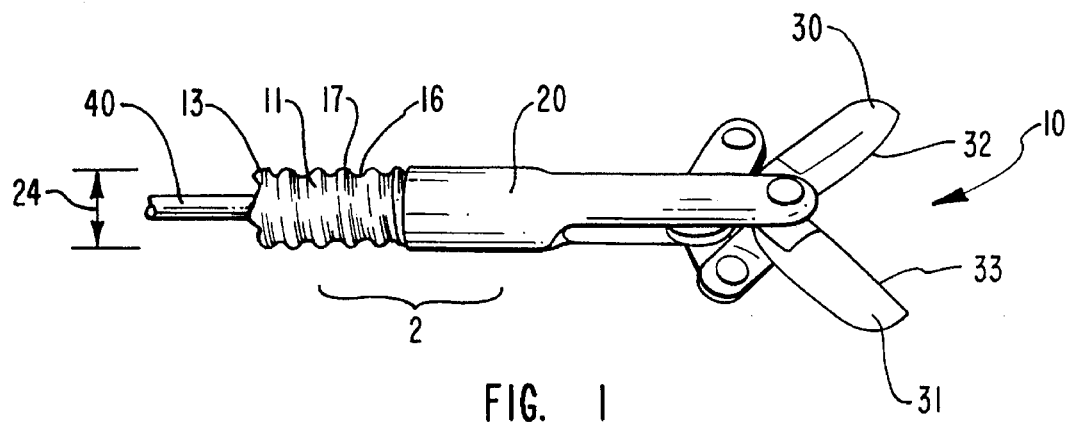
FIG. 1 is a side view of presently-preferred embodiment of the invention.
Figure 2:
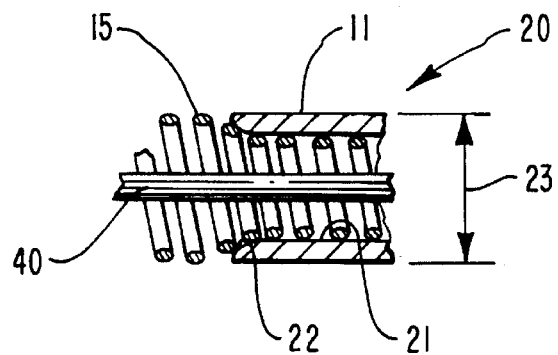
FIG. 2 is an axial cross-section of the portion marked "2" in FIG. 1.

A biopsy forceps 10 according to this invention includes a support cable 11. The support cable has a distal end 12 and a proximal end 13. The support cable is a flexible metal helically wound wire structure having coil convolutions 15 with a groove 16 between adjacent convolutions, and a curved crest 17 at the maximum diameter of the convolutions. The convolutions abut each other closely, but they are not attached to one another. The support cable can lengthen, and its diameter can be reduced. In this invention, the diameter is reduced, and the support cable lengthens locally and slightly to enable it.

A jaw mount 20 has a socket with an internal wall 21. Wall 21 is cylindrical, although it may also have a short bellmouth section 22 or internal bevel to provide a lead-in for the cable. The diameter 23 of the cylindrical portion is smaller than the maximum diameter 24 of the convolutions of the support cable.

Jaws 30, 31 are hingedly mounted to the jaw mount. They have respective sharp cutting edges 32, 33, which when brought against or past each other will cut the specimen loose. For this purpose each has a respective lever arm 34, 35 connected to a control wire 40. The control wire extends through the passage in the support cable.

The instrument is assembled by inserting the control wire into the passage. Then, when the socket of the jaw mount reaches the distal end of the support cable, it is rotated while being axially pressed over the distal end. This will slightly compress the coiled structure, and the cable passes along the support cable very much like a threaded movement, except that there is no thread.

Figure 3:
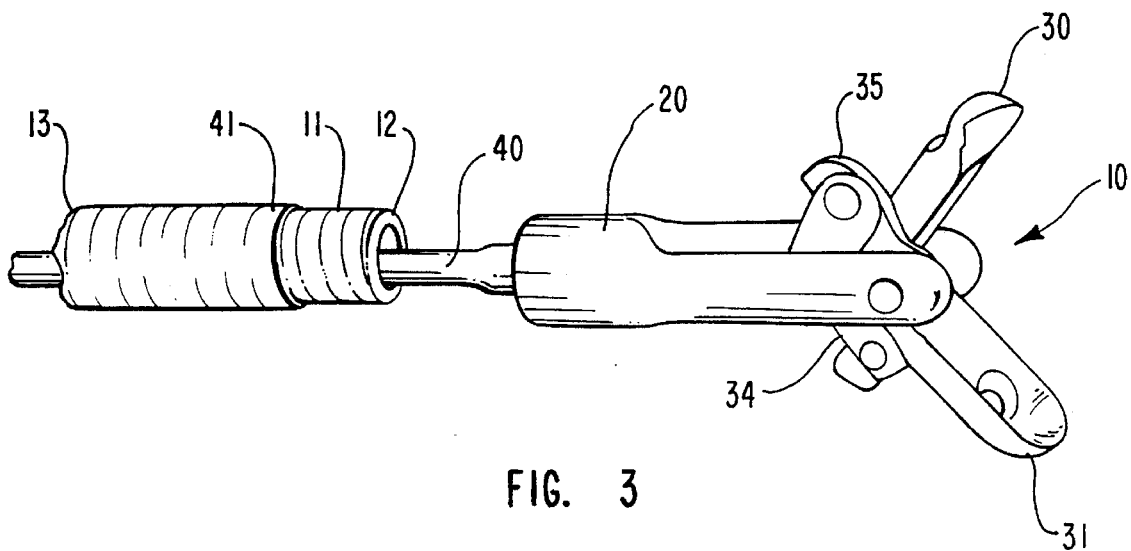
FIG. 3 is a fragmentary view showing the embodiment of FIG. 1 disassembled.

Retention of the jaw mount is quite reliable, because of the substantial spring-back force exerted radially by the convolutions against the inside wall of the jaw mount. The amount of compression varies with the dimensions and characteristics of the support cable. A cable having an external diameter of about 2 mm, will generally be compressed diametrically by about 5%, the support cable being a wound stainless steel wire. The dimensions of the mount will be selected so its outer diameter will be about equal to that of the support cable. Often the support cable will have a coating 41 (FIG. 3) of Teflon or some other plastic. It will be stripped from the cable over the inserted length. The outer diameter of the mount and of the layer will be approximately equal.

Accordingly, a flexible biopsy forceps can be provided whose most expensive parts can be cleaned, and which requires the replacement only of a relatively inexpensive length of cable when it is to be cleaned and reused.

This invention is not to be limited by the embodiment shown in the drawings and described in the description, which is given by way of example and not of limitation, but only in accordance with the scope of the appended claims.

I claim:

1. A biopsy forceps comprising:

disposable cable means for providing bendable steering and support for a reusable forceps instrument assembly, said cable means comprising a helically wound wire having distal and proximal ends and forming a continuous passage therethrough from the distal to the proximal end; and a reusable forceps instrument assembly comprising:

a control wire passing through said passage and having proximal and distal ends;

forceps instrument means at the distal end of said control wire and operative in response to movement of said control wire to effect a surgical procedure; and unitary mounting means to which said forceps instrument means is operatively mounted at one end thereof, said mounting means comprising a socket means at an opposite end thereof for selective coupling and uncoupling to the distal end of said helically wound wire by rotating the distal end of said helical wire into or out of said socket means such that said cable means can be uncoupled from said mounting means and discarded, and said reusable forceps assembly, including said control wire, said forceps instrument means and mounting means can be resterilized and reused with another cable means.

2. A biopsy forceps according to claim 1 in which a bell-mounted portion is provided on an inner wall of the socket means to facilitate entry of said distal end of the helical wire.

3. A biopsy forceps according to claim 1 in which said forceps instrument means comprises a pair of jaws pivotally mounted for movement toward and away from one another, said control wire being connected to said jaws to cause said pivotal movement as the consequence of axial movement in the passage.

* * * * *

UNITED STATES PATENT AND TRADEMARK OFFICE
CERTIFICATE OF CORRECTION

PATENT NO. : 5,578,056
DATED : November 26, 1996
INVENTOR(S) : Georg Pauldrach

It is certified that error appears in the above-indentified patent and that said Letters Patent is hereby corrected as shown below:

Column 4, Line 31, "bell-mounted" should be --bell-mouthed--

Signed and Sealed this

Sixteenth Day of September, 1997

Attest:

BRUCE LEHMAN

Attesting Officer

Commissioner of Patents and Trademarks